(12) United States Patent
Barham et al.

(10) Patent No.: US 9,545,065 B2
(45) Date of Patent: Jan. 17, 2017

(54) WATERMELON VARIETIES

(71) Applicant: New Avenue Productions, Inc., Gilroy, CA (US)

(72) Inventors: Robert Barham, Gilroy, CA (US); Laura Barham Brown, Gilroy, CA (US)

(73) Assignee: NEW AVENUE PRODUCTIONS, INC., Gilroy, CA (US)

( * ) Notice: Subject to any disclaimer, the term of this patent is extended or adjusted under 35 U.S.C. 154(b) by 144 days.

(21) Appl. No.: 14/203,417

(22) Filed: Mar. 10, 2014

(65) Prior Publication Data

US 2014/0283163 A1    Sep. 18, 2014

Related U.S. Application Data

(60) Provisional application No. 61/799,174, filed on Mar. 15, 2013.

(51) Int. Cl.
  *A01H 5/08*  (2006.01)
  *A01H 5/10*  (2006.01)
  *A01H 4/00*  (2006.01)

(52) U.S. Cl.
  CPC . *A01H 5/08* (2013.01); *A01H 4/00* (2013.01)

(58) Field of Classification Search
  CPC ...................................................... A01H 5/08
  See application file for complete search history.

(56) References Cited

PUBLICATIONS

All-American Selections (Watermelon 'Harvest Moon' F1 2013 AAS Vegetable Award Winner, available online Dec. 23, 2012).*
All-American Selections—With Internet Archive Data (Watermelon 'Harvest Moon' F1 2013 AAS Vegetable Award Winner, available online Dec. 23, 2012).*

* cited by examiner

*Primary Examiner* — Lee A Visone
(74) *Attorney, Agent, or Firm* — Morrison & Foerster LLP

(57) ABSTRACT

The present invention relates to methods of producing unique varieties of triploid watermelon with diverse rind patterning. More specifically, a new watermelon variety designated 'Harvest Moon' is described. 'Harvest Moon' is a seedless, spotted watermelon variety with improved flesh quality and deeper red color than traditional spotted watermelon varieties.

11 Claims, 2 Drawing Sheets
(2 of 2 Drawing Sheet(s) Filed in Color)

FIG. 1

| Rind Pattern | Comparison Type | Picture |
|---|---|---|
| Dark Green | Sugar Baby | |
| Gray | Mickey Lee | |
| Mottled Stripe | Crimson Sweet | |
| Tiger Stripe | Jubilee | |
| Check Stripe | Navajo Sweet | |
| Spotted | Heirloom Moon and Stars | |

WATERMELON VARIETIES

CROSS REFERENCE TO RELATED APPLICATION

This application claims the benefit under 35 §USC 119(e) of prior U.S. Provisional Patent Application No. 61/799,174, filed Mar. 15, 2013, the disclosure of which is hereby incorporated by reference in its entirety.

FIELD OF THE INVENTION

The present invention relates to the field of plant breeding. In particular, this invention relates to new and distinctive varieties of watermelon, *Citrullus lanatus*.

BACKGROUND OF THE INVENTION

All cultivated forms of watermelon belong to the polymorphic species *Citrullus lanatus*. As a crop, watermelons are grown commercially wherever environmental conditions permit the production of an economically viable yield. Cultivated watermelons grow as annual plants with large, broad leaves. The leaves may be lobed or simple and are typically orbicular to triangular-ovate in shape. The flowers are monoecious, producing both male and female flowers. The flesh color of cultivated watermelons is red, yellow, or white with ovate to oblong strongly compressed seeds that may be brown or white in color. The characterization of the mature fruit can vary widely among varieties of watermelon. Fruits may be round to oblong or elliptical with rind colors varying from dark green to yellow and rind patterning varying widely.

Many changes that occurred with the domestication of the watermelon relate to fruit morphology, with a specialization in fruit shape, size, and flavor. Cultivated watermelons can vary from 5 to 45 pounds, depending on the variety. In the United States, watermelon is grown in at least 44 states, but the principal watermelon growing states are Georgia, Florida, Texas, and California. Asia is the largest producer of watermelon, with 83.4% of the world production in 2011. Fresh watermelons are consumed in many forms, generally fresh, sliced, or as an ingredient in prepared foods. Over 80% of watermelons grown in the United States are triploid seedless varieties, preferred for their ease of consumption, increased yield, and premium market value over diploid seeded varieties.

*Citrullus lanatus* is a member of the family Cucurbitaceae. The Cucurbitaceae is a family of about 90 genera and 700 to 760 species, mostly of the tropics. The family includes melons, pumpkins, squashes, gourds, cucumber, loofah and many weeds. The genus *Citrullus*, to which the watermelon belongs, consists of 4 species, including *C. colocynthis*, *C. rehmii*, and *C. ecirrhosus*, all of which may be crossed with each other successfully. The watermelon is believed to be native to southern Africa and has been cultivated there for about 4000 years.

Regular, seeded watermelon has eleven pairs of chromosomes ($2n=2x=22$). There also exist tetraploid varieties, which have 44 chromosomes in their somatic cells ($2n=4x=44$). Popular "seedless" varieties are triploid, meaning they have 33 chromosomes in their somatic cells ($3x=33$) and are derived from a cross between male diploid and female tetraploid parents. Triploid plants are unable to produce viable gametes; therefore, when triploid plants are grown in the presence of diploid plants, the triploid plants produce seedless fruit. These seedless varieties may sometimes produce fruit with small, edible white ovules, similar to those in immature cucumbers.

Watermelon is an important and valuable field crop. Watermelon may have a wide variety of rind colorations and patterns, from solid green to yellow, to striped, mottled, or spotted. Generally, these traits are naturally-occurring, and fruit exhibiting such patterning may or may not contain the desired attributes of a high-yield, high-quality watermelon suitable for commercial production. Thus, there is a need to provide a diverse array of rind patterning for commercially viable fruits.

SUMMARY OF THE INVENTION

In order to meet these needs, the present invention is directed to improved fruit quality of spotted watermelons. In one embodiment, the present invention is directed to a triploid watermelon plant having a rind patterned with spots, produced by crossing two parent watermelon plants with at least one parent exhibiting the plant trait characterized by spotted foliage and spots on fruit rind. In one embodiment, the present invention is directed to triploid plants. In yet another embodiment, the present invention is directed to tetraploid plants.

In one embodiment, the present invention is directed to a triploid watermelon variety, *Citrullus lanatus*, seed designated as 'Harvest Moon' having ATCC Accession Number PTA-122198. In one embodiment, the present invention is directed to a *Citrullus lanatus* watermelon plant and parts isolated therefrom produced by growing 'Harvest Moon' watermelon seed. In another embodiment, the present invention is directed to a *Citrullus lanatus* plant and parts isolated therefrom having all the physiological and morphological characteristics of a *Citrullus lanatus* plant produced by growing 'Harvest Moon' watermelon seed having ATCC Accession Number PTA-122198. In still another embodiment, the present invention is directed to an $F_1$ hybrid *Citrullus lanatus* watermelon seed, plants grown from the seed, and fruit isolated therefrom having a watermelon plant characterized by producing spotted cotyledons, leaves, and fruit as a parent.

Watermelon plant parts include watermelon leaves, ovules, pollen, seeds, watermelon fruits, parts of watermelon fruits, flowers, cells, and the like. In another embodiment, the present invention is further directed to watermelon leaves, ovules, pollen, seeds, watermelon fruits, parts of watermelon fruits, and/or flowers isolated from 'Harvest Moon' watermelon plants. In certain embodiments, the present invention is further directed to pollen or ovules isolated from 'Harvest Moon' watermelon plants. In another embodiment, the present invention is further directed to protoplasts produced from 'Harvest Moon' watermelon plants. In another embodiment, the present invention is further directed to tissue culture of 'Harvest Moon' watermelon plants, and to watermelon plants regenerated from the tissue culture, where the plant has all of the morphological and physiological characteristics of 'Harvest Moon' watermelon. In certain embodiments, tissue culture of 'Harvest Moon' watermelon plants is produced from a plant part selected from leaf, anther, pistil, stem, petiole, root, root tip, fruit, seed, flower, cotyledon, hypocotyl, embryo and meristematic cell.

In yet another embodiment, the present invention is further directed to a method of selecting watermelon plants, by a) growing 'Harvest Moon' watermelon plants where the 'Harvest Moon' plants are grown from watermelon seed having ATCC Accession Number PTA-122198 and b) selecting a plant from step a). In another embodiment, the present invention is further directed to watermelon plants, plant parts and seeds produced by the watermelon plants where the watermelon plants are isolated by the selection method of the invention.

In an exemplary embodiment, the present invention is directed to a method of producing triploid watermelon variety 'Harvest Moon' by crossing a male, diploid, 'Moon and Stars' watermelon with any female, tetraploid, watermelon that produces dark fruit. In another embodiment, the present invention is directed to a method of producing a triploid watermelon variety resembling 'Harvest Moon' by crossing a diploid male 'Moon and Stars' watermelon with a tetraploid 'Moon and Stars' female. In yet another embodiment, the present invention is directed to a method of producing a triploid watermelon variety resembling 'Harvest Moon' by crossing a diploid male watermelon that produces dark fruit with a tetraploid 'Moon and Stars' female.

In another embodiment, the present invention is directed to a method of creating triploid watermelon plants with spotted rinds by crossing a diploid spotted watermelon plant, such as the exemplary variety 'Moon and Stars', with any tetraploid watermelon plant, wherein the progeny triploid watermelon plants would produce seedless fruit with rind patterning incorporating both the diploid and tetraploid parent rind patterning and spots. In yet another embodiment, the present invention is directed to a method of creating triploid watermelon plants with spotted rinds by crossing a tetraploid spotted watermelon plant with any diploid watermelon plant, wherein the progeny triploid watermelon plants would produce seedless fruit with rind patterning incorporating both the tetraploid and diploid rind patterning and spots.

According to the invention, there is provided a watermelon plant designated 'Harvest Moon'. This invention thus relates to the seeds of watermelon 'Harvest Moon', to the plants of watermelon 'Harvest Moon', and to methods for producing a watermelon plant containing in its genetic material one or more transgenes and to the transgenic watermelon plants produced by that method. This invention also relates to methods for producing other watermelon cultivars or hybrids derived from watermelon 'Harvest Moon' and to the watermelon cultivars and hybrids derived by the use of those methods.

In another embodiment, the present invention is directed to methods for producing a watermelon plant containing in its genetic material one or more transgenes and to the transgenic watermelon plant produced by those methods.

In another embodiment, the present invention is directed to single gene converted plants of watermelon 'Harvest Moon'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring watermelon gene or a transgene introduced through genetic engineering techniques.

In another embodiment, the present invention is directed to methods for developing watermelon plants in a watermelon plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See, Pierce et al., *HortScience* (1990) 25:605-615; Wehner, T., *Cucurbit Genetics Cooperative Report*, (1997) 20: 66-88; and Kennard et al., *Theorical Applied Genetics* (1994) 89:217-224). Seeds, watermelon plants, and parts thereof produced by such breeding methods are also part of the invention.

In another embodiment, the present invention s directed to methods of making a watermelon variety having yellow spots, the method comprising crossing a female tetraploid watermelon plant with a male diploid yellow-spotted watermelon plant. In a further embodiment, the present invention is directed to methods of making a watermelon variety having yellow spots, the method comprising crossing a female tetraploid yellow-spotted watermelon plant with a male diploid watermelon plant. In a further embodiment, the present invention is directed to methods of making a watermelon variety having yellow spots, the method comprising crossing a female tetraploid yellow-spotted watermelon plant with a male diploid yellow-spotted watermelon plant.

In one embodiment, the present invention is directed to triploid watermelon seeds wherein said seed germinates and produces a watermelon fruit comprising at least one yellow spot of a diameter of at least 0.2 cm. In further embodiments, the present invention is directed to watermelon plants, and parts thereof, produced by growing triploid watermelon seeds wherein said seed germinates and produces a watermelon fruit comprising at least one yellow spot of a diameter of at least 0.2 cm.

In additional embodiments, the present invention is directed to watermelon seeds resulting from methods making a watermelon variety of the present invention. In additional embodiments, the present invention is directed to watermelon plants, and parts thereof, obtained from growing the seeds of the present invention. In additional embodiments, the present invention is directed to watermelon plants, and parts thereof, having all the physiological and morphological characteristics of the watermelon plants of the present invention. In additional embodiments, the present invention is directed to watermelon tissue culture, obtained from the plants of the present invention. In further embodiments, the tissue culture of the present invention is produced from a plant part selected from the group consisting of leaf, anther, pistil, stem, petiole, root, root tip, fruit, seed, flower, cotyledon, hypocotyl, embryo and meristematic cell.

In addition to the exemplary aspects and embodiments described above, further aspects and embodiments will become apparent by reference by study of the following descriptions.

BRIEF DESCRIPTION OF THE FIGURES

The patent or application file contains at least one drawing executed in color. Copies of this patent or patent application publication with color drawings will be provided by the office upon request and payment of the necessary fee.

FIG. 1 depicts exemplary types of watermelon plants and rind patterns.

DETAILED DESCRIPTION OF THE INVENTION

Figure 2:
FIG. 2 depicts an exemplary rind patterning of watermelon variety 'Harvest Moon' fruits.

The present invention is directed towards triploid varieties of watermelon exhibiting desired and/or unique rind patterning. This unique rind patterning can be accomplished by crossing two watermelon plants such that the progeny watermelon plants exhibit rind patterning of both parent plants. In an exemplary embodiment, the present invention is directed towards triploid, seedless, watermelon plans. Triploid plants are produced by the cross of a diploid male and tetraploid female. Genes exhibited by triploid plants can be thought of as contributed by the parents in "doses." By way of example, if a diploid (2x) spotted plant A is crossed with a tetraploid (4x) plant B, the result of the cross would be triploid (3x) plant C, wherein plant C receives one set of genes from A and two sets of genes from B. It can be said that, in this exemplary cross, that plant C has one "dose" of genes from plant A and two "doses" of genes from plant B. By this model, dominant genes can be transferred to progeny in a dose-dependent manner.

The gene associated with watermelon spotting is Sp. The Sp gene is dominant and may be transferred to offspring in the manner set forth above. Spotted triploids with one Sp gene (one-dose) exhibit less spotting than do spotted triploids with three Sp genes (three-dose); therefore, it is possible to customize the quantity of spotting on the resulting watermelon fruit by controlling the dosage of the spotting gene. Exemplary combinations for making triploid watermelon plants with varying dosages of spotted genes are described in Table I-A, Table I-B, and Table I-C. Although the Sp gene can confer spotting to the watermelon rind, the spotting is not rind-specific, but rather is present over the entirety of the plant, including rind, leaves, and cotyledons. The spotting is a separable trait from rind patterning and when one or more Sp genes is/are introduced from one parent via a cross; spots are present in the progeny, in addition to whatever rind pattern is present on the other parent.

Table I-A shows exemplary combinations for making triploid spotted watermelon plants from diploid male spotted watermelon plants and tetraploid female non-spotted watermelon plants (hereafter referred to as "1-dose" spotted triploids). Table I-B shows exemplary combinations for making triploid spotted watermelon plants from tetraploid female spotted watermelon plants and diploid male non-spotted watermelon plants (hereafter referred to as "2-dose" spotted triploids). Table I-C shows exemplary combinations for making triploid spotted watermelon plants from diploid male spotted watermelon plants and tetraploid female spotted watermelon plants (hereafter referred to as "3-dose" spotted triploids). Exemplary varieties of watermelon exhibiting the described rind patterning may be found in FIG. 1.

TABLE I-A

Exemplary Combinations for Making 1-dose Spotted Triploids

| | | Male (2n) Rind Pattern | | | | | |
|---|---|---|---|---|---|---|---|
| | | Spotted on Dark Green Background | Spotted on Medium Green Background | Spotted on Gray Background | Spotted on mottled stripe Background | Spotted on Tiger Stripe Background | Spotted on Check Stripe Background |
| Female (4n) Rind Pattern | Dark Green | x | x | x | x | x | x |
| | Medium Green | x | x | x | x | x | x |
| | Gray | x | x | x | x | x | x |
| | Mottled Stripe | x | x | x | x | x | x |
| | Tiger Stripe | x | x | x | x | x | x |
| | Check Stripe | x | x | x | x | x | x |

TABLE I-B

Exemplary Combinations for Making 2-dose Spotted Triploids

| | | Male (2n) Rind Pattern | | | | | |
|---|---|---|---|---|---|---|---|
| | | Dark Green | Medium Green | Gray | Mottled Stripe | Tiger Stripe | Check Stripe |
| Female (4n) Rind Pattern | Spotted on Dark Green Background | x | x | x | x | x | x |
| | Spotted on Medium Green Background | x | x | x | x | x | x |
| | Spotted on Gray Background | x | x | x | x | x | x |
| | Spotted on mottled stripe Background | x | x | x | x | x | x |
| | Spotted on Tiger Stripe Background | x | x | x | x | x | x |
| | Spotted on Check Stripe Background | x | x | x | x | x | x |

TABLE I-C

Exemplary Combinations for Making 3-dose Spotted Triploids

|  |  | Male (2n) Rind Pattern | | | | | |
|---|---|---|---|---|---|---|---|
|  |  | Spotted on Dark Green Background | Spotted on Medium Green Background | Spotted on Gray Background | Spotted on mottled stripe Background | Spotted on Tiger Stripe Background | Spotted on Check Stripe Background |
| Female (4n) Rind Pattern | Spotted on Dark Green Background | x | x | x | x | x | x |
|  | Spotted on Medium Green Background | x | x | x | x | x | x |
|  | Spotted on Gray Background | x | x | x | x | x | x |
|  | Spotted on mottled stripe Background | x | x | x | x | x | x |
|  | Spotted on Tiger Stripe Background | x | x | x | x | x | x |
|  | Spotted on Check Stripe Background | x | x | x | x | x | x |

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and through selection varieties or parent lines are developed. The goal is to combine in a single variety or hybrid an improved combination of desirable traits from the parental germplasm. These important traits may include higher yield, field performance, fruit and agronomic quality such as fruit shape and length, resistance to diseases and insects, and tolerance to drought and heat.

Choice of breeding or selection methods can depend on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for at least three years. The best lines can then be candidates for new commercial cultivars. Those still deficient in a few traits may be used as parents to produce new populations for further selection. These processes, which lead to the final step of marketing and distribution, may take from ten to twenty years from the time the first cross or selection is made.

One goal of watermelon plant breeding is to develop new, unique, and genetically superior watermelon cultivars and hybrids. A breeder can initially select and cross two or more parental lines, followed by repeated selfing and selection, producing many new genetic combinations. A plant breeder can then select which germplasms to advance to the next generation. These germplasms may then be grown under different geographical, climatic, and soil conditions, and further selections can be made during, and at the end of, the growing season.

The development of commercial watermelon cultivars thus requires the development of watermelon parental lines, the crossing of these lines, and the evaluation of the crosses. Pedigree breeding and recurrent selection breeding methods may be used to develop cultivars from breeding populations. Breeding programs can be used to combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into watermelon varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., *Theor. Appl. Genet.*, 77:889-892, 1989.

Additional non-limiting examples of breeding methods that may be used include, without limitation, those found in *Principles of Plant Breeding*, John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999.

DEFINITIONS

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Androecious plant. A plant having staminate flowers only.

Backcrossing. Backcrossing is a process in which a breeder repeatedly crosses hybrid progeny back to one of the parents, for example, a first generation hybrid $F_1$ with one of the parental genotype of the $F_1$ hybrid.

Blossom end. The blossom end is the distal end of the fruit (the "far" end as measured from the base of the plant) where the flower blossom is located. The other end of a fruit is the stem end.

Blossom scar. The blossom scar is the small mark left on the distal end of the fruit after the flower falls off.

Covered cultivation. Any type of cultivation where the plants are not exposed to direct sunlight. The covering includes but is not limited to greenhouses, glasshouses, nethouses, plastic houses and tunnels.

Essentially all the physiological and morphological characteristics. A plant having essentially all the physiological and morphological characteristics means a plant having the physiological and morphological characteristics of the recurrent parent, except for the characteristics derived from the converted gene.

Gene. As used herein, "gene" refers to a segment of nucleic acid. A gene can be introduced into a genome of a species, whether from a different species or from the same species, using transformation or various breeding methods.

Gynoecious plant. A plant having pistillate flowers only.

Monoecious plant. A plant having separate staminate and pistillate flowers on the same plant.

Percent Identity. Percent identity as used herein refers to the comparison of the homozygous alleles of two watermelon lines, hybrids or varieties. Percent identity is determined by comparing a statistically significant number of the homozygous alleles of two developed varieties, lines or hybrids. For example, a percent identity of 90% between watermelon plant 1 and watermelon plant 2 means that the two plants have the same allele at 90% of their loci.

Percent Similarity. Percent similarity as used herein refers to the comparison of the homozygous alleles of a watermelon plant such as hybrid watermelon 'Harvest Moon' with another plant, and if the homozygous allele of hybrid watermelon 'Harvest Moon' matches at least one of the alleles from the other plant then they are scored as similar. Percent similarity is determined by comparing a statistically significant number of loci and recording the number of loci with similar alleles as a percentage. A percent similarity of 90% between hybrid watermelon 'Harvest Moon' and another plant means that hybrid watermelon 'Harvest Moon' matches at least one of the alleles of the other plant at 90% of the loci.

Propagate. To "propagate" a plant means to reproduce the plant by means including, but not limited to, seeds, cuttings, divisions, tissue culture, embryo culture or other in vitro method.

Quantitative Trait Loci (QTL). Quantitative trait loci refer to genetic loci that control to some degree numerically representable traits that are usually continuously distributed.

Regeneration. Regeneration refers to the development of a plant from tissue culture.

Seedless. Seedless plants refer to triploid watermelon plants that produce fruit without viable seeds. These fruit may be devoid of seeds or seed-like structures, or may contain immature white ovules.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique, genetic engineering or mutation.

Transgene. A "transgene" is a gene taken or copied from one organism and inserted into another organism. A transgene may be a gene that is foreign to the receiving organism or it may be a modified version of a native, or endogenous, gene.

Overview of the Exemplary Watermelon Variety 'Harvest Moon'

Watermelon 'Harvest Moon' is a triploid yellow-spotted watermelon with superior characteristics. 'Harvest Moon' watermelons are intended for cultivation from spring to autumn, or whenever environmentally possible. Watermelon cultivar 'Harvest Moon' is resistant to sunburn.

As depicted in FIG. 2, 'Harvest Moon' watermelon plants produce seedless fruit having a dark green color with modest yellow spots, and a round shape. Fruit of the watermelon variety 'Harvest Moon' has a smooth rind, and crisp, fine, non-fibrous red flesh.

Additionally, watermelon variety 'Harvest Moon' has shown uniformity and stability for the traits, within the limits of environmental influence for the traits. No variant traits have been observed or are expected in 'Harvest Moon'.

Objective Description of the Variety 'Harvest Moon'

Watermelon variety 'Harvest Moon' has the following morphologic and other characteristics:

General fruit type: Round large; dark green rind with modest yellow spots; red flesh Area of best adaptation: Most U.S. Areas Maturity:

Number of days from emergence to anthesis: 40

Number of days from pollination to maturity: 38

80 days relative maturity

Maturity Category Medium

Ploidy: Triploid; seedless

Plant:

Cotyledon shape: Flat

Plant sex form: Monoecious

Number of main stems at crown: 3

Number of flowers per plant at first fruit set: 7 staminate, 3 pistillate, 0 perfect Stem:

Stem shape: Round

Diameter at second node: 8 mm

Stem surface: Pubescent

Vine length (at last harvest): 121 cm

Number of internodes (at last harvest): 6

Leaf:

Leaf shape: Round

Leaf lobes: Lobed

Leaf length: 15 cm

Leaf width: 15 cm

Leaf size: Length-width equal

Dorsal surface pubescence: Pubescent

Ventral surface pubescence: Pubescent

Leaf color: Medium green

Flower:

2.5 cm diameter across staminate 2.3 cm diameter across pistillate n/a diameter across perfect Flower color: Yellow Mature fruit:

Shape: oval

Length: 33 cm

Diameter at midsection: 28 cm

Average weight: 8.6 kg

Maximum fruit weight: 9.0 kg

Index=length+diameter×10: 12

Fruit surface: Smooth

Skin color pattern: Spots

Primary color: Dark green

Secondary color: Yellow

Rind:

Rind texture: Tough

Flesh:

Flesh texture: Crisp

Flesh coarseness: Fine—little fiber

Flesh color: Red

Seed:

Seed size: Medium

Disease resistance:

Anthracnose: Untested

Downy mildew: Untested

*Fusarium* wilt: Untested

Gummy stem blight: Untested

Squash mosaic: Untested

Powdery mildew: Untested

Watermelon mosaic: Untested

Other resistance:
Sunburn: Resistant
Root knot: Untested

FURTHER EMBODIMENTS

This invention also is directed to methods for producing a watermelon plant by crossing a first parent watermelon plant with a second parent watermelon plant wherein either the first or second parent watermelon plant produces spotted fruit.

As used herein, the term plant includes plant cells, plant protoplasts, plant cell tissue cultures from which watermelon plants can be regenerated, plant calli, plant clumps and plant cells that are intact in plants or parts of plants, such as embryos, pollen, ovules, flowers, leaves, stems, and the like.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed cultivar.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed watermelon plants, using transformation methods as described below to incorporate transgenes into the genetic material of the watermelon plant(s).

Expression Vectors for Watermelon Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin (Fraley et al., Proc. Natl. Acad. Sci. U.S.A., 80:4803 (1983)). Another commonly used selectable marker gene is the hygromycin phosphotransferase gene which confers resistance to the antibiotic hygromycin (Vanden Elzen et al., Plant Mol. Biol., 5:299 (1985)).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate or bromoxynil (Comai et al., Nature 317:741-744 (1985), Gordon-Kamm et al., Plant Cell 2:603-618 (1990) and Stalker et al., Science 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include .alpha.-glucuronidase (GUS), .alpha.-galactosidase, luciferase and chloramphenicol, acetyltransferase (Jefferson, R. A., Plant Mol. Biol. Rep. 5:387 (1987), Teeri et al., EMBO J. 8:343 (1989), Koncz et al., Proc. Natl. Acad. Sci. U.S.A. 84:131 (1987), DeBlock et al., EMBO J. 3:1681 (1984)).

In vivo methods for visualizing GUS activity that do not require destruction of plant tissues are available (Molecular Probes publication 2908, IMAGENE GREEN, p. 1-4 (1993) and Naleway et al., J. Cell Biol. 115:151 a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., Science 263:802 (1994)). GFP and mutants of GFP may be used as screenable markers.

Expression Vectors for Watermelon Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in watermelon. Optionally, the inducible promoter is operably linked to a nucleotide sequence encoding a signal sequence which is operably linked to a gene for expression in watermelon. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Meft et al., Proc. Natl. Acad. Sci. U.S.A. 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in watermelon or the constitutive promoter is operably linked to a nucleotide sequence encoding a signal sequence which is operably linked to a gene for expression in watermelon.

Many different constitutive promoters can be utilized in the instant invention. Exemplary constitutive promoters include, but are not limited to, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO 96/30530.

C. Tissue-Specific or Tissue-Preferred Promoters

A tissue-specific promoter is operably linked to a gene for expression in watermelon. Optionally, the tissue-specific promoter is operably linked to a nucleotide sequence encoding a signal sequence which is operably linked to a gene for expression in watermelon. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is watermelon. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology, CRC Press, Boca Raton 269:284 (1993).

Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See for example, Shoresh, et al., "Characterization of a Mitogen-Activated Protein Kinase Gene from Watermelon Required for *Trichoderma*-Conferred Plant Resistance", Plant Physiol. November 2006; 142(3): 1169-1179 (activation of *Trichoderma*-induced MAPK (TIPK) gene is necessary for the plant's *Trichoderma*-conferred defense against bacterial pathogens); Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt delta-endotoxin gene. Moreover, DNA molecules encoding .delta.-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes; and Atsushi, et al., "Possible Involvement of Leaf Gibberellins in the Clock-Controlled Expression of XSP30, a Gene Encoding a Xylem Sap Lectin, in Watermelon Roots" Plant Physiol. December 2003; 133(4): 1779-1790.

D. A vitamin-binding protein such as avidin. See PCT application US 93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* .alpha.-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper-accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO 95/16776 (disclosure of peptide derivatives of tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, watermelon mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-.alpha.-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

R. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in Transgenic Research. 1999, 8: 1, 33-44 that discloses *Lactuca sativa* resistant to glufosinate. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Accl-S1, Accl-S2 and Accl-S3 genes described by Marshall et al., Theor. Appl. Genet. 83:435 (1992).

C. An herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Increased iron content of the watermelon, for example by transforming a plant with a soybean ferritin gene as described in Goto et al., Acta Horticulturae. 2000, 521, 101-109.

B. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

C. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus lichenifonnis* .alpha.-amylase), Elliot et al., Plant Molec. Biol. 21:515 (1993) (nucleotide sequences of tomato invertase genes), SOgaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

4. Genes that Control Male-Sterility

A. Introduction of a deacetylase gene under the control of a tapetum-specific promoter and with the application of the chemical N—Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

5. Genes that Create a Site for Site Specific DNA Integration.

This includes the introduction of FRT sites that may be used in the FLP/FRT system and/or Lox sites that may be used in the Cre/LoxP system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104; International publication numbers WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. publication number 2004/0148654 and international publication number WO 01/36596 where abscisic acid is altered in plants resulting in improved plant phenotype such as increased yield and/or increased tolerance to abiotic stress; international publication numbers WO 2000/006341, WO 04/090143; U.S. application Ser. No. 10/817,483 and U.S. Pat. No. 6,992,237 where cytokinin expression is modified resulting in plants with increased stress tolerance, such as drought tolerance, and/or increased yield. Also see international publication numbers WO 02/02776, WO 2003/052063; JP2002281975; U.S. Pat. No. 6,084,153; international publication number WO 01/64898; U.S. Pat. Nos. 6,177,275 and 6,107,547 (enhancement of nitrogen utilization and altered nitrogen responsiveness). For ethylene alteration, see U.S. publication numbers 2004/0128719, U.S. 2003/0166197 and international publication number WO 2000/32761. For plant transcription factors or transcriptional regulators of abiotic stress, see e.g. U.S. publication numbers 2004/0098764 or U.S. 2004/0078852.

Other genes and transcription factors that affect plant growth and agronomic traits such as yield, flowering, plant growth and/or plant structure, can be introduced or introgressed into plants, see e.g. international publication numbers WO 97/49811 (LHY), WO 98/56918 (ESD4), WO 97/10339; U.S. Pat. No. 6,573,430 (TFL), U.S. Pat. No. 6,713,663 (FT); international publication numbers WO 96/14414 (CON), WO 96/38560, WO 01/21822 (VRN1), WO 00/44918 (VRN2), WO 99/49064 (GI), WO 00/46358 (FRI), WO 97/29123; U.S. Pat. No. 6,794,560, U.S. Pat. No. 6,307,126 (GAI), and international publication numbers WO 99/09174 (D8 and Rht), and WO 2004/076638 and WO 2004/031349 (transcription factors).

Methods for Watermelon Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227:1229 (1985), Curtis et al., Journal of Experimental Botany. 1994, 45: 279, 1441-1449, Tones et al., Plant cell Tissue and Organic Culture. 1993, 34: 3, 279-285, Dinant et al., Molecular Breeding. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao, F. J. L., et al. Pl. Cell. Rep. 12(9, July), 483-490 (1993). Aragao, Theor. Appl. Genet. 93: 142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p. 53 (1990); D'Halluin et al., Plant Cell 4:1495-1505 (1992) and Spencer et al., Plant Mol. Biol. 24:51-61 (1994). See also Chupean et al., Biotechnology. 1989, 7: 5, 503-508.

Following transformation of watermelon target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic watermelon line. Alternatively, a genetic trait which has been engineered into a particular watermelon cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et al., "An Integrated Genetic Linkage Map of the Soybean Genome" Crop Science 39:1464-1490 (1999), and Berry et al., "Assessing Probability of Ancestry Using Simple Sequence Repeat Profiles: Applications to Maize Inbred Lines and Soybean Varieties" Genetics 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for watermelon variety 'Harvest Moon.'

The present invention comprises a watermelon plant characterized by molecular and physiological data obtained from the representative sample of said variety deposited with the American Type Culture Collection (ATCC). Further provided by the invention is a watermelon plant formed by the combination of the disclosed watermelon plant or plant cell with another watermelon plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for watermelon plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the watermelon lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to overexpress. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

Single-Gene Conversions

When the terms watermelon plant, cultivar, hybrid or watermelon line are used in the context of the present invention, this also includes any single gene conversions of that line. The term "single gene converted plant" as used herein refers to those watermelon plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental watermelon plants for that line, backcrossing 1, 2, 3, 4, 5, 6, 7, 8 or more times to the recurrent parent. The parental watermelon plant which contributes the gene for the desired characteristic is termed the nonrecurrent or donor parent. This terminology refers to the fact that the nonrecurrent parent is used one time in the backcross protocol and therefore does not recur. The parental watermelon plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

Tissue Culture

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a triploid watermelon plant by crossing a tetraploid parent watermelon plant with a diploid parent watermelon plant wherein the first and/or second parent watermelon plant is a watermelon plant characterized by producing fruits with a spotted rind and by having spotted foliage. In this manner, a diverse array of watermelon rind patterns may be developed and selected for superior qualities including taste, yield, and hardiness. Further, both tetraploid and diploid parent watermelon plants can come from watermelon plants characterized by producing fruits with a spotted rind.

In an exemplary method, to produce watermelon variety 'Harvest Moon,' a 'Moon and Stars' (a yellow-spotted diploid watermelon variety) male is crossed with a generic dark green tetraploid female such as, experimental tetraploid NAP 9505, resulting in a triploid 'Harvest Moon' F1 progeny. Advantageously, the 'Moon and Stars' watermelon plant (or any diploid spotted watermelon plant) could be used in crosses with other, different, tetraploid watermelon plants to produce the first generation ($F_1$) hybrid triploid watermelon seeds and plants with superior characteristics and spotting similar to 'Harvest Moon.' Methods exist in the art to produce similar diploid or tetraploid progeny.

The cultivar of the invention can also be used for transformation where exogenous genes are introduced and expressed by the cultivar of the invention. Genetic variants of 'Harvest Moon' created either through traditional breeding methods or through transformation of hybrid watermelon 'Harvest Moon' by any of a number of protocols known to those of skill in the art are intended to be within the scope of this invention.

The following describes breeding methods that may be used with watermelon variety 'Moon and Stars' (or other equivalent spotted watermelon variety) in the development of further watermelon plants. One such embodiment is a method for developing hybrid watermelon plants in a watermelon plant breeding program comprising: obtaining the watermelon plant, or a part thereof, of a watermelon plant characterized by producing fruits with a spotted rind, utilizing said plant or plant part as a source of breeding material, and selecting a watermelon progeny plant with molecular markers in common with the parent watermelon and/or with morphological and/or physiological characteristics attributed to progeny of a spotted watermelon plant cross, such as variety 'Harvest Moon'. Breeding steps that may be used in the watermelon plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

One of ordinary skill in the art of plant breeding would know how to evaluate the traits of two plant varieties to determine if there is no significant difference between the two traits expressed by those varieties. For example, see Fehr and Walt, Principles of Cultivar Development, p. 261-286 (1987). Thus the invention includes watermelon plants comprising a combination of at least two 'Harvest Moon' traits selected from the 'Harvest Moon' combination of traits listed in the Summary of the Invention, so that said progeny watermelon plant is not significantly different for said traits than watermelon 'Harvest Moon' as determined at the 5% significance level when grown in the same environmental conditions and/or may be characterized by percent similarity or identity to hybrid watermelon 'Harvest Moon' as determined by SSR markers. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

As used herein, the term "plant" includes plant cells, plant protoplasts, plant cell tissue cultures from which watermelon plants can be regenerated, plant calli, plant clumps and plant cells that are intact in plants or parts of plants, such as leaves, pollen, embryos, cotyledons, hypocotyl, roots, root tips, anthers, pistils, flowers, seeds, stems and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the hybrid watermelon 'Harvest Moon' is maintained by K&B Development LLC having offices located at: 10030 New Avenue, Gilroy, Calif. 95020. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, (ATCC), P.O. Box 1549, MANASSAS, Va. 20108 USA.

At least 2500 seeds of hybrid watermelon 'Harvest Moon' were deposited on Jun. 5, 2015 according to the Budapest Treaty in the American Type Culture Collection (ATCC), ATCC Patent Depository, 10801 University Boulevard, Manassas, Va., 20110, USA. The deposit has been assigned ATCC number PTA-122198. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed.

The deposit will be maintained in the ATCC depository, which is a public depository, for a period of 30 years, or 5 years after the most recent request, or for the effective life of the patent, whichever is longer, and will be replaced if a deposit becomes nonviable during that period.

The invention claimed is:

1. A seed of watermelon variety 'Harvest Moon', representative sample of seed having been deposited under ATCC Accession Number PTA-122198.

2. A watermelon plant produced by growing the seed of claim 1.

3. A plant part from the plant of claim 2, wherein said part is a leaf, an ovule, pollen, a fruit, a cell, or a portion thereof.

4. A watermelon plant having all the physiological and morphological characteristics of the watermelon plant of claim 2.

5. A plant part from the plant of claim 4, wherein said part is a leaf, an ovule, pollen, a fruit, a cell, or a portion thereof.

6. Pollen or an ovule of the plant of claim 2.

7. A protoplast produced from the plant of claim 2.

8. A tissue culture of the plant of claim 2, wherein said tissue culture is produced from a plant part selected from the group consisting of leaf, anther, pistil, stem, petiole, root, root tip, fruit, flower, cotyledon, hypocotyl, and meristematic cell.

9. A watermelon plant regenerated from the tissue culture of claim 8, wherein the plant comprises all of the morphological and physiological characteristics of watermelon variety 'Harvest Moon', representative sample of seed of said variety having been deposited under ATCC Accession Number PTA-122198.

10. The plant part of claim 3, wherein said part is a fruit.
11. The plant part of claim 5, wherein said part is a fruit.

\* \* \* \* \*